United States Patent [19]

Vancheri et al.

[11] 4,099,939
[45] Jul. 11, 1978

[54] SPILL-PROOF GAS SAMPLER

[75] Inventors: Frank J. Vancheri; Stanley P. Nebash, both of Pittsburgh; Paul W. McConnaughey, Wilkinsburg, all of Pa.

[73] Assignee: Mine Safety Appliances Company, Pittsburgh, Pa.

[21] Appl. No.: 817,365

[22] Filed: Jul. 20, 1977

[51] Int. Cl.² ............................................ B01D 47/02
[52] U.S. Cl. ................................. 55/246; 23/254 R; 55/256; 55/270; 73/421.5 R; 261/121 R
[58] Field of Search ................ 55/246, 255, 256, 270; 73/421.5 R; 261/121 R; 23/254 R

[56] References Cited
U.S. PATENT DOCUMENTS

| 355,594 | 1/1887 | Daimler | 55/256 X |
|---|---|---|---|
| T941,014 | 12/1975 | Charron et al. | 261/DIG. 67 X |
| 1,820,512 | 8/1931 | Varvel | 55/255 X |
| 2,297,934 | 10/1942 | Baily | 55/246 |
| 2,612,745 | 10/1952 | Vecchio | 55/256 X |
| 3,001,402 | 9/1961 | Koblin | 73/421.5 R |
| 3,522,734 | 8/1970 | Curby | 55/256 X |
| 3,960,523 | 6/1976 | Ryan | 55/270 X |

FOREIGN PATENT DOCUMENTS

| 45,675 | 11/1935 | France | 261/121 R |

Primary Examiner—Frank W. Lutter
Assistant Examiner—Kathleen J. Prunner
Attorney, Agent, or Firm—Brown, Flick & Peckham

[57] ABSTRACT

A bubbler bottle has an upper chamber and a lower chamber of smaller diameter than the upper chamber. A central inlet tube extends from near the bottom of the lower chamber up through the upper chamber and the top of the bottle. An exhaust tube extends from near one side of the inlet tube laterally out through the side of the upper chamber, with its outer end adapted to be connected to a suction pump for drawing contaminated air down through the inlet tube and out of its lower end into a predetermined volume of liquid in the lower chamber. The liquid is spaced from a collar which encircles the inlet tube and is sealed to the side of the upper chamber below the exhaust tube but with clearance around the inlet tube. The capacity of the lower chamber is such that the liquid remaining in it when the bottle is on its side is beneath the inlet tube, and the capacity of the upper chamber is such that when the bottle is inverted all of the liquid in the inverted upper chamber will be below the exhaust tube. When the bottle is turned back on its side, the inner end of the exhaust tube will always be above the liquid in the upper chamber.

4 Claims, 9 Drawing Figures

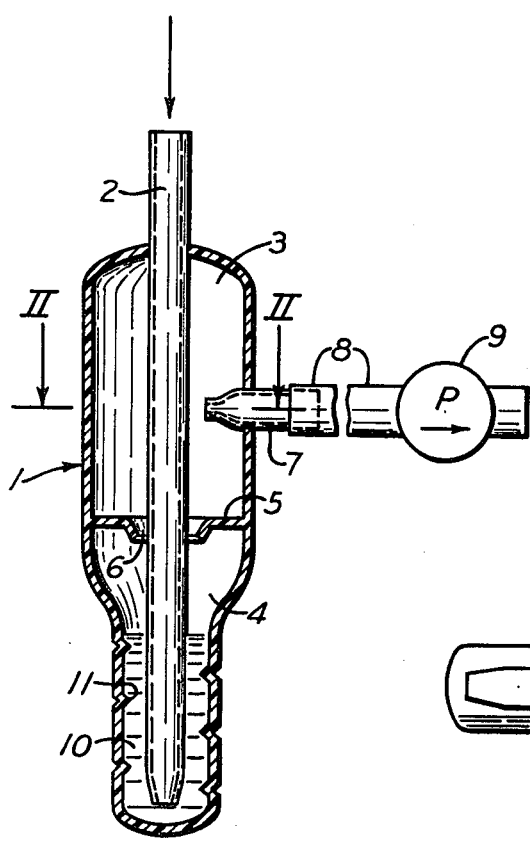
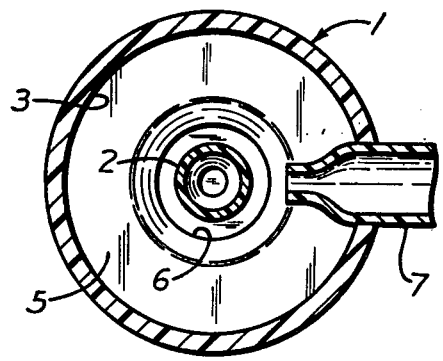
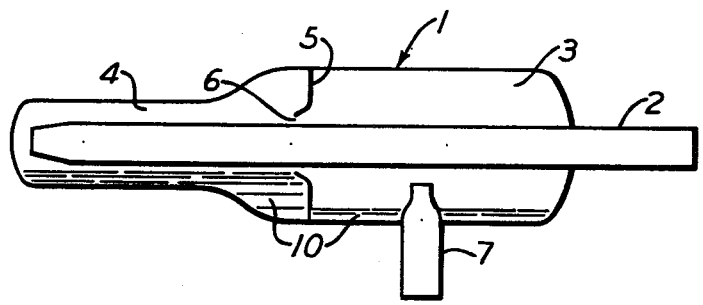
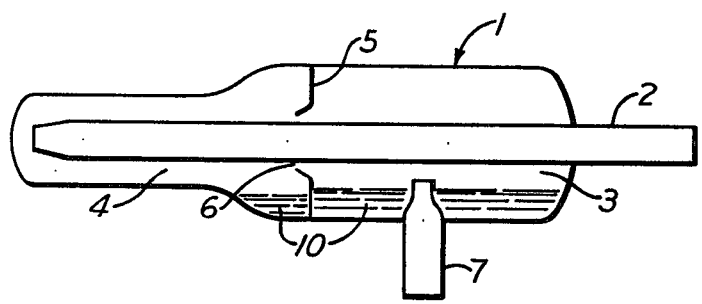
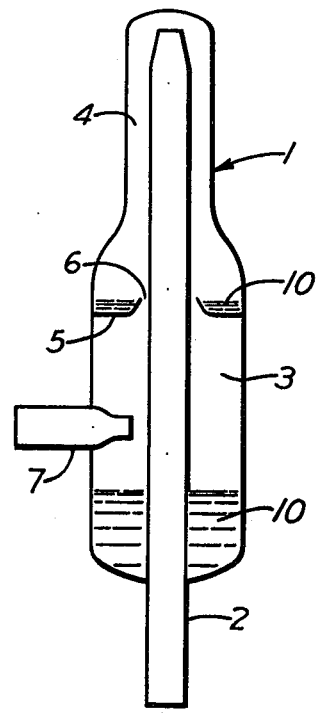

SPILL-PROOF GAS SAMPLER

This invention is concerned with a miniature gas sampler that can be worn by a person during work for sampling contaminated air or any other gas containing a pollutant that can be adsorbed in a liquor sorbent.

It is among the objects of this invention to provide a gas sampler which is a single inexpensive unit, which is compact and only a few inches long, which can be attached to the clothing of a man at work, and which is of such construction that the liquid within it will not escape regardless of the position of the sampler.

The invention is illustrated in the accompanying drawings, in which

FIG. 1 is a vertical section;

FIG. 2 is an enlarged cross section taken on the line II—II of FIG. 1;

FIGS. 3, 4 and 5 are diagrams showing the sampler in different positions; and

Figure 6:
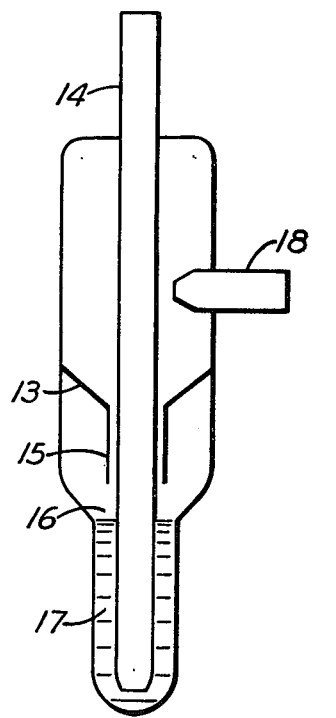
FIGS. 6 to 9 are diagrams of a modification shown in four different positions.

Referring to the preferred embodiment of the invention shown in FIGS. 1 and 2 of the drawings, the bubbler includes a normally upright bottle 1, preferably made of glass or transparent plastic. The lower portion of the bottle most suitably has a smaller diameter than the upper portion. Extending from near the bottom of the bottle up through the top there is a central inlet tube 2. It is sealed in the top of the bottle, by which it is supported. The bottle is divided into upper and lower chambers 3 and 4 by means of a collar 5 that encircles the inlet tube in the lower part of the larger upper portion of the bottle and is sealed to the side of the bottle. The opening through the collar is slightly larger than the tube so that there is clearance between them to provide a passage 6 between the two chambers. Although the collar can be flat, it is preferred to provide it with a slight downturned lip. An exhaust tube 7 is sealed in the side of the upper chamber 3, with the inner end of the tube near one side of the central inlet tube. The outer end of the exhaust tube can be connected by a flexible tube 8 to a battery-operated suction pump 9 for drawing a gas, such as contaminated air, for example, down through the inlet tube and out of its lower end. The pump is a standard item.

The lower chamber 4 of the bubbler contains a predetermined volume of a sorbent solution 10, through which it is desired that the contaminated gas should bubble. The liquid may be water or any other suitable sorbent. Its depth will depend upon the glass being treated, which can be any gas containing a pollutant that can be adsorbed in a liquid sorbent, but the lower end of the inlet tube 2 must be located beneath the surface of the liquid. The gas drawn through the bubbler may be, for example, air contaminated with anticholinesterase inhibitors such as phosphate and phosphate ester pesticides that may be present in low concentrations. The contaminated air bubbles up through the liquid, which removes the contaminants. Indentations 11 in the side of the reduced lower portion of the bottle help to break up the bubble path.

It is a feature of this invention that the capacity of the lower chamber 4 of the bubbler is such that when the bubbler is turned on its side as shown in FIG. 3, some of the liquid will remain in the lower chamber and all of it will be beneath the inlet tube 2. The rest of the liquid may pass through the central passage 6 and into the upper chamber. It will be seen that in this position all of the liquid is beneath the outlet of the inlet tube and the inlet of the exhaust tube 7.

Even though the bottle is inverted as shown in FIG. 4, the capacity of the upper chamber 3 is such that all of the liquid in that chamber will be below the exhaust tube and, of course, below the outlet of the inlet tube. If the bottle is then turned back on its side as shown in FIG. 5, the upper level of the liquid in the upper chamber will still remain below the inlet of the exhaust tube.

Consequently, no matter what position the bottle is in, none of the liquid will escape through the inlet tube or be drawn into the exhaust tube by the pump. The gas sampler disclosed herein is intended to be attached to the clothing of a worker who also carries the suction pump on his belt or in some other convenient way. Since the sampler is spill-proof, it continues to function regardless of the motions of the worker. Even though he bends over, twists or lies on his back, the liquid in the bubbler will not escape. By preventing the liquid from running out of the bottle or being sucked into the pump, there is no danger of ruining the test, which may have to extend over an eight hour period.

Figure 7:
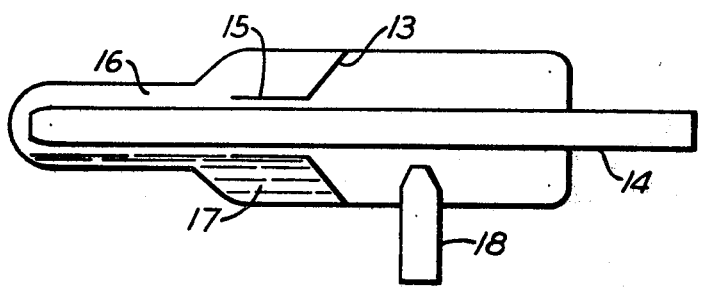
Figure 9:
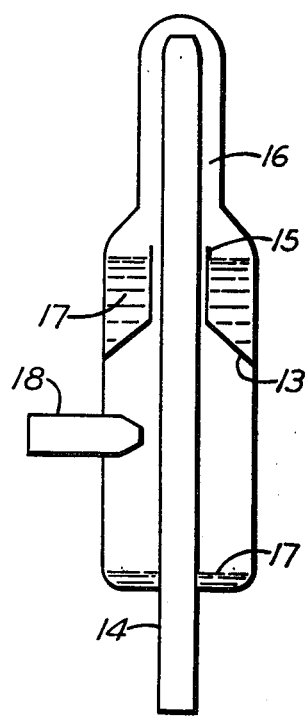
Figure 8:
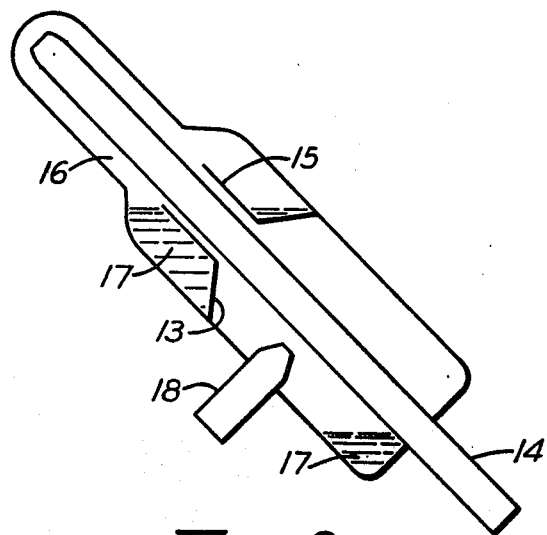

In the modification shown in FIG. 6, the bubbler includes the same basic parts as the one just described, but the collar 13 that encircles the inlet tube 14 includes a tubular portion 15 that extends down into the lower chamber 16. This forms a receptacle around the inlet tube when the bubbler is inverted as shown in FIG. 9, so that most of the liquid 17 is retained in the inverted lower chamber by the collar. Consequently, there is no danger of any of the liquid being drawn into the exhaust tube 18. When the bubbler is in a horizontal position as in FIG. 7, all of the liquid in the lower chamber remains beneath the inlet tube so that it cannot escape through that tube. If the bubbler is tilted as shown in FIG. 8, most of the liquid will remain above the collar and no liquid will be able to escape through either tube.

According to the provisions of the patent statutes, we have explained the principle of our invention and have illustrated and described what we now consider to represent its best embodiment. However, we desire to have it understood that, within the scope of the appended claims, the invention may be practiced otherwise than as specifically illustrated and described.

We claim:

1. A spill-proof gas sampler in the form of a bubbler comprising a normally upright bottle having an upper portion and a lower portion, a central inlet tube extending from near the bottom of the bottle up through the top of the bottle, a collar encircling the inlet tube in the lower part of said upper portion and sealed to the side of the bottle to divide it into upper and lower chambers, there being clearance between the collar and inlet tube to provide a restricted passage between said chambers, an exhaust tube above said collar extending from near one side of said inlet tube laterally out through the side of the bottle, said tubes being sealed in the bottle, and a predetermined volume of liquid in said lower chamber spaced from said collar, the depth of the liquid in said lower chamber being such that the lower end of said inlet tube is located beneath the surface of the liquid, the capacity of said lower chamber being such that all of the liquid remaining therein when the bottle is on its side is beneath the inlet tube, and the capacity of the upper chamber is such that when the bottle is inverted all of the liquid in that chamber will be below the exhaust tube and when the bottle is turned back on its side from its inverted position the inner end of the exhaust tube will always be above the liquid in said upper chamber.

2. A spill-proof gas sampler according to claim 1, in which said collar includes a tubular portion extending toward said lower chamber and forming the outer wall of said passage.

3. A spill-proof gas sampler according to claim 1, in which the side wall of said lower chamber is provided with inwardly projecting portions.

4. A spill-proof gas sampler according to claim 1, in which said lower portion of the bottle has a smaller diameter than said upper portion.

* * * * *